(12) United States Patent
Rieping et al.

(10) Patent No.: US 7,575,905 B2
(45) Date of Patent: Aug. 18, 2009

(54) PROCESS FOR L-AMINO ACID PRODUCTION USING ENTEROBACTERIACEAE STRAINS WITH ENHANCED YIBD

(75) Inventors: Mechthild Rieping, Bielefeld (DE); Nicole Dusch, Werther (DE)

(73) Assignee: Evonik Degussa GmbH, Essen (DE)

( * ) Notice: Subject to any disclaimer, the term of this patent is extended or adjusted under 35 U.S.C. 154(b) by 622 days.

(21) Appl. No.: 10/794,417

(22) Filed: Mar. 8, 2004

(65) Prior Publication Data

US 2005/0176112 A1 Aug. 11, 2005

(30) Foreign Application Priority Data

Feb. 6, 2004 (DE) .................. 10 2004 005 836

(51) Int. Cl.
C12P 13/04 (2006.01)
C12P 13/08 (2006.01)
C12P 13/06 (2006.01)
C12P 13/12 (2006.01)
C12N 1/12 (2006.01)

(52) U.S. Cl. .................. 435/106; 435/252.1; 435/115; 435/116; 435/113

(58) Field of Classification Search .................. None
See application file for complete search history.

(56) References Cited

U.S. PATENT DOCUMENTS 4,278,765 A * 7/1981 Debabov et al. ............ 435/481
5,705,371 A * 1/1998 Debabov et al. ............ 435/115

FOREIGN PATENT DOCUMENTS

| DE | 101 32 946 A1 | 7/2001 |
|---|---|---|
| DE | 101 35 053 A1 | 7/2001 |
| EP | 0 271 838 A2 | 6/1988 |
| EP | 0 994 190 A2 | 4/2000 |
| EP | 1 013 765 A1 | 6/2000 |
| EP | 1 149 911 A2 | 10/2001 |
| WO | WO 99/18228 | 4/1999 |
| WO | WO 99/53035 | 10/1999 |
| WO | WO 01/05939 A1 | 1/2001 |
| WO | WO 01/92545 A1 | 12/2001 |
| WO | WO 02/06459 A1 | 1/2002 |

(Continued)

OTHER PUBLICATIONS

Tamayo et al. (2002) Infection and Immunity, vol. 70(12), pp. 6770-6778.*

(Continued)

*Primary Examiner*—Rebecca E Prouty
*Assistant Examiner*—Alexander D Kim
(74) *Attorney, Agent, or Firm*—Law Office of: Michael A. Sanzo, LLC

(57) ABSTRACT

The invention relates to a process for the preparation of L-amino acids by the fermentation of recombinant microorganisms of the family Enterobacteriaceae. The microorganisms produce the desired L-amino acid and overexpress the *E. coli* or *S. typhimurium* yibD gene encoding the putative glycosyl transferase enzyme. The microorganisms are cultivated in a medium under conditions in which the desired L-amino acid is enriched in the medium or in the cells. The amino acid is then isolated, optionally with constituents of the fermentation broth, and/or all or part ($\geq 0$ to 100%) of the biomass.

20 Claims, 1 Drawing Sheet

Map of plasmid pTrc99AyibD

FOREIGN PATENT DOCUMENTS

| | | |
|---|---|---|
| WO | WO 02/29080 A2 | 4/2002 |
| WO | WO 02/36797 A2 | 5/2002 |
| WO | WO 02/064808 A1 | 8/2002 |
| WO | WO 02/077183 | 10/2002 |
| WO | WO 02/081698 A2 | 10/2002 |
| WO | WO 02/081721 A2 | 10/2002 |
| WO | WO 02/081722 A2 | 10/2002 |
| WO | WO 03/004598 A2 | 1/2003 |
| WO | WO 03/004663 A2 | 1/2003 |
| WO | WO 03/004664 A2 | 1/2003 |
| WO | WO 03/004665 A2 | 1/2003 |
| WO | WO 03/004669 A2 | 1/2003 |
| WO | WO 03/004670 A2 | 1/2003 |
| WO | WO 03/004671 A2 | 1/2003 |
| WO | WO 03/004674 A2 | 1/2003 |
| WO | WO 03/006666 A2 | 1/2003 |
| WO | WO 03/008603 A2 | 1/2003 |
| WO | WO 03/008604 A2 | 1/2003 |
| WO | WO 03/008605 A2 | 1/2003 |
| WO | WO 03/008606 A2 | 1/2003 |
| WO | WO 03/008607 A2 | 1/2003 |
| WO | WO 03/008608 A2 | 1/2003 |
| WO | WO 03/008609 A2 | 1/2003 |
| WO | WO 03/008610 A2 | 1/2003 |
| WO | WO 03/008612 A2 | 1/2003 |
| WO | WO 03/008613 A2 | 1/2003 |
| WO | WO 03/008614 A2 | 1/2003 |
| WO | WO 03/008615 A2 | 1/2003 |
| WO | WO 03/038106 A2 | 5/2003 |
| WO | WO 03/076635 A1 | 9/2003 |
| WO | WO 03/076637 | 9/2003 |

OTHER PUBLICATIONS

Steinberg et al. (1997) Antimicrobial Agents and Chemotherapy, vol. 41, pp. 1738-1742.*

Epelbaum et al (1998) Journal of Bacteriology, vol. 180, pp. 4056-4067.*

Theze et al. (1974) Journal of Bacteriology, vol. 118, pp. 990-998.*

Riley et al. (1990) Nucleic Acids Research, vol. 18, pp. 2887-2890.*

Blattner et al. (1997) Science, vol. 277, pp. 14531462.*

Burland et al. (1993) Nucleic Acids Research, vol. 21, pp. 3385-3390.*

Lee et al (2005) Journal of Bacteriology, vol. 187, p. 1124-1134.*

Jin et al. (2001) Glycoconjugate Journal, vol. 18, p. 779-787.*

McClelland et al. (2001) Nature, vol. 413, pp. 852-856.*

Hermann, et al., "Improved L-Threonine Production with *Escherichia coli*," *Proceedings of European Congress Biotechnology*, XX, XX, Aug. 24, 2003, p. 85.

Lehninger, et al., *Principles of Biochemistry*, Worth Publishers, $2^{nd}$ Edition, pp. 697-715 (1997).

McClelland, et al., "Complete Genome Sequence of *Salmonella enterica* Serovar Typhimurium LT2," *Nature* 413:852-856 (2001).

Sofia, et al., "Analysis of the *Escherichia coli* Genome. V. DNA Sequence of the Region from 76.0 to 81.5 Minutes," *Nucleic Acid Res.* 22(13):2576-2586 (1994).

Database UniProt 'Online!', Jul. 1, 1898, "Putative Glycosyl Transferase yibD (EC 2.-.-.-)," XP-002324637.

Database EMBL 'Online!', Jun. 2, 1994, "E. Coli Chromosomal Region from 76.0 to 81.5 Minutes," XP-00234368.

Database EMBL 'Online!', Oct. 29, 2001, "Salmonella Tphyimurium LT2, Section 176 of 220 of the Complete Genome," XP-002324369.

Andrews, et al., "Cloning, Sequencing, and Mapping of the Bacterioferritin Gene (*bfr*) of *Escherichia coli* K-12," *J. Bacteriol.* 171:3940-3947 (1989).

Blankenhorn, et al., "Acid- and Base-Induced Proteins during Aerobic and Anaerobic Growth of *Escherichia coli* Revealed by Two-Dimensional Gel Electrophoresis," *J. Bacteriol.* 181:2209-2216 (1999).

Blattner, et al., "The Complete Genome Sequence of *Escherichia coli* K-12," *Science* 277:1453-1462 (1997).

Boos, et al., "Maltose/Maltodextrin System of *Escherichia coli*: Transport, Metabolism, and Regulation," *Microbiol. Mol. Biol. Rev.* 62:204-229 (1998).

Brune, et al., "Cloning and Sequencing of the Adenylate Kinase Gene (*adk*) of *Escherichia coli*," *Nucleic Acids Res.* 13:7139-7151 (1985).

Carrier, et al., "Library of Synthetic 5' Secondary Structures to Manipulate mRNA Stability in *Escherichia coli*," *Biotechnol. Prog.* 15:58-64 (1999).

Clarke, et al., "Nucleotide Sequence of the *pntA* and *pntB* Genes Encoding the Pyridine Nucleotide Transhydrogenase of *Escherichia coli*," *Eur. J. Biochem.* 158:647-653 (1986).

Cole, et al., "The Nucleotide Sequence of the *malT* Gene Encoding the Positive Regulator of *Escherichia coli* Maltose Regulon," *Gene* 42:201-208 (1986).

Danot, "A Complex Signaling Module Governs the Activity of MalT, the Prototype of an Emerging Transactivator Family," *Proc. Natl. Acad. Sci. USA* 98:435-440 (2001).

DiRusso, "Nucleotide Sequence of the *fadR* Gene, a Multifunctional Regulator of Fatty Acid Metabolism in *Escherichia coli*," *Nucleic Acids Res.* 16:7995-8009 (1988).

Enos-Berlage, et al., "Complex Metabolic Phenotypes Caused by a Mutation in *yigF*, Encoding a Member of the Highly Conserved YER057c/YjgF Family of Proteins," *J. Bacteriol.* 180:6519-6528 (1998).

Fountoulakis, et al., "Enrichment of Low Abundance Proteins of *Escherichia coli* by Hydroxyapatite Chromatography," *Electrophoresis* 20:2181-2195 (1999).

Franch, et al., "U-Turns and Regulatory RNAs," *Curr. Opin. Microbiol.* 3:159-164 (2000).

Garrido-Pertierra, "Isolation and Properties of *Salmonella typhimurium* Mutants Defective in Enolase," *Revista Española de Fisiologia* 36:33-40 (1980).

Gulick, et al., "Evolution of Enzymatic Activities in the Enolase Superfamily: Crystal Structures of the L-Ala-D/L-Glu Epimerases from *Escherichia coli* and *Bacillus subtilis*," *Biochemistry* 40:15716-15724 (2001).

Heim, et al., "Cloning an *Escherichia coli* Gene Encoding a Protein Remarkably Similar to Mammalian Aldehyde Dehydrogenases," *Gene* 99:15-23 (1991).

Hofnung, Divergent Operons and the Genetic Structure of the Maltose B Region in *Escherichia coli* K12, *Genetics* 76:169-187 (1974).

Hogg, et al., "Nucleotide Sequence and Analysis of the *mgl* Operon of *Escherichia coli* K12," *Mol. Gen. Genet.* 229:453-459 (1991).

Jensen, et al., "Artificial Promoters for Metabolic Optimization," *Biotechnol. Bioeng.* 58:191-195 (1998).

Kaga, et al., "Rnase G-Dependent Degradation of the *eno* mRNA Encoding a Clycolysis Enzyme Enolase in *Escherichia coli*," *Biosci. Biotechnol. Biochem.* 66:2216-2220 (2002).

Kirkpatrick, et al., "Acetate and Formate Stress: Opposite Responses in the Proteome of *Escherichia coli*," *J. Bacteriol.* 183:6466-6477 (2001).

Klein, et al., "Cloning, Nucleotide Sequence, and Functional Expression of the *Escherichia coli* Enolase (*eno*) Gene in a Temperature-Sensitive *eno* Mutant Strain," *J. Seq. Mapping* 6:351-355 (1996).

Knappe, et al., "A Radical-Chemical Route to Acetyl-CoA: The Anaerobically Induced Pyruvate Formate-Lyase System of *Escherichia coli*," *FEMS Microbiol. Rev.* 75:383-398 (1990).

Komatsubara, et al., "Transductional Construction of a Threonine-Producing Strain of *Serratia marcescens*," *Appl. Environ. Microbiol.* 38:1045-1051 (1979).

Landgraf, et al., "The Role of H-NS in One Carbon Metabolism," *Biochimie* 76:1063-1070 (1994).

Lee, et al., "Global Analysis of Transcriptomes and Proteomes of a Parent Strain and an L-Threonine-Overproducing Mutant Strain," *J. Bacteriol.* 185:5442-5451 (2003).

MacPherson, et al., "Identification of the GalP Galactose Transport Protein of *Escherichia coli*," *J. Biol. Chem.* 258:4390-4396 (1983).

Martin, et al., "Forskolin Specifically Inhibits the Bacterial Galactose-$H^+$ Transport Protein, GalP," *J. Biol. Chem.* 269:24870-24877 (1994).

Masuda, et al., "Improvement of Nitrogen Supply for L-Threonine Production by a Recombinant Strain of *Serratia marcescens*," *Appl. Biochem. Biotechnol.* 37:255-265 (1992).

McPherson, et al., "Complete Nucleotide Sequence of the *Escherichia coli gdhA* Gene," *Nucleic Acids Res.* 11:5257-5267 (1983).

Meyer, et al., Molecular Characterization of Glucokinase from *Escherichia coli* K-12, *J. Bacteriol.* 179:1298-1306 (1997).

Missiakas, et al., "Modulation of the *Escherichia coli* $\sigma^E$ (RpoE) Heat-Shock Transcription-Factor Activity by the RseA, RseB and RseC Proteins," *Mol. Microbiol.* 24:355-371 (1997).

Nagelkerke, et al., "2-Deoxygalactose, a Specific Substrate of the *Salmonella typhimurium* Galactose Permease: Its Use for the Isolation of *galP* Mutants," *J. Bacteriol.* 133:607-613 (1978).

Niersbach, et al., "Cloning and Nucleotide Sequence of the *Escherichia coli* K-12 *ppsA* Gene, Encoding PEP Synthase," *Mol. Gen. Genet.* 231:332-336 (1992).

Parsons, et al., "Solution Structure and Functional Ligand Screening of HI0719, a Highly Conserved Protein from Bacteria to Humans in the YjgF/YER057c/UK114 Family," *Biochemistry* 42:80-89 (2003).

Postma, "Galactose Transport in *Salmonella typhimurium*," *J. Bacteriol.* 129:630-639 (1977).

Qiu, et al., "The *Escherichia coli polB* Locus Is Identical to *dinA*, the Structural Gene for DNA Polymerase II," *J. Biol. Chem.* 272:8611-8617 (1997).

Raibaud, et al., "Maltotriose Is the Inducer of the Maltose Regulon of *Escherichia coli*," *J. Bacteriol.* 169:3059-3061 (1987).

Raibaud, et al., "Essential and Nonessential Sequences in *malPp*, a Positively Controlled Promoter in *Escherichia coli*," *J. Bacteriol.* 161:1201-1208 (1985).

Ravnikar, et al., "Structural and Functional Analysis of a Cloned Segment of *Escherichia coli* DNA That Specifies Proteins of a $C_4$ Pathway of Serine Biosynthesis," *J. Bacteriol.* 169:4716-4721 (1987).

Reyes, et al., "Overproduction of MalK Protein Prevents Expression of the *Escherichia coli mal* Regulon," *J. Bacteriol.* 170:4598-4602 (1988).

Richet, et al., "MalT, the Regulatory Protein of the *Escherichia coli* Maltose System, Is an ATP-Dependent Transcriptional Activator," *EMBO J.* 8:981-987 (1989).

Rödel, et al., "Primary Structures of *Escherichia coli* Pyruvate Formate-Lyase and Pyruvate-Formatre-Lyase-Activating Enzyme Deduced from the DNA Nucleotide Sequences," *Eur. J. Biochem.* 177:153-158 (1988).

Romeo, et al., "Identification and Molecular Characterization of *csrA*, a Pleiotropic Gene from *Escherichia coli* That Affects Glycogen Biosynthesis, Gluconeogenesis, Cell Size, and Surface Properties," *J. Bacteriol.* 175:4744-4755 (1993).

Sabe, et al., "Molecular Cloning of the Phosphoenolpyruvate Carboxylase Gene, *ppc*, of *Escherichia coli*," *Gene* 31:279-283 (1984).

Schlegel, et al., "Network Regulation of the *Escherichia coli* Maltose System," *J. Mol. Microbiol. Biotechnol.* 4:301-307 (2002).

Schmitz, et al., "Reduced Transaminase B (IlvE) Activity Caused by the Lack of *yjgF* Is Dependent on the Status of Threonine Deaminase (IlvA) in *Salmonella enterica* Serovar Typhimurium," *J. Bacteriol.* 186:803-810 (2004).

Schreiber, et al., "A New Mechanism for the Control of Prokaryotic Transcriptional Regulator: Antagonistic Binding of Positive and Negative Effectors," *Mol. Microbiol.* 35:765-776 (2000).

Spring, et al., "The Purification and Characterization of *Escherichia coli* Enolase," *J. Biol. Chem.* 246:6797-6802 (1971).

Stephens, et al., "The Pyruvate Dehydrogenase Complex of *Escherichia coli* K-12—Nucleotide Sequence Encoding the Pyruvate Dehydrogenase Component," *Eur. J. Biochem.* 133:155-162 (1983).

Stephens, et al., "The Pyruvate Dehydrogenase Complex of *Escherichia coli* K12—Nucleotide Sequence Encoding the Dihydrolipoamide Acetyltransferase Component," *Eur. J. Biochem.* 133:481-489 (1983).

Stephens, et al., "Nucleotide Sequence of the Lipoamide Dehydrogenase Gene of *Escherichia coli* K12," *Eur. J. Biochem.* 135:519-527 (1983).

Sugita, et al., "Cloning and Characterization of the Mutated Threonine Operon (*thrA₁5A₂5BC*) of *Serratia marcescens*," *Gene* 57:151-158 (1987).

Sunnarborg, et al., "Regulation of the Glyoxylate Bypass Operon: Cloning and Characterization of *iclR*," *J. Bacteriol.* 172:2642-2649 (1990).

Suzuki, et al., "Mapping, Cloning, and DNA Sequencing of *pepB* Which Encodes Peptidase B of *Escherichia coli* K-12," *J. Ferment. Bioeng.* 82:392-397 (1996).

Thorsness, et al., "Inactivation of Isocitrate Dehydrogenase by Phosphorylation Is Mediated by the Negative Charge of the Phosphate," *J. Biol. Chem.* 262:10422-10425 (1987).

Valle, et al., "Nucleotide Sequence of the Promoter and Amino-Terminal Coding Region of the Glutamate Dehydrogenase Structural Gene of *Escherichia coli*," *Gene* 23:199-209 (1983).

Venter, et al., "Molecular Dissection of Membrane-Transport Proteins: Mass Spectrometry and Sequence Determination of the Galactose-$H^+$ Symport Protein, GalP, of *Escherichia coli* and Quantitative Assay of the Incorporation of [ring-$2^{13}C$]histidine and $^{15}NH_3$," *Biochem J.* 363:243-252 (2002).

Vidal-Ingigliardi, et al., "A Small C-Terminal Region of the *Escherichia coli* MalT Protein Contains the DNA-Binding Domain," *J. Biol. Chem.* 268:24527-24530 (1993).

Vogel, et al., "Cloning and Sequenc of the *mdh* Structural Gene of *Escherichia coli* Coding for Malate Dehydrogenase," *Arch. Microbiol.* 149:36-42 (1987).

Volz, "A Test Case for Structure-Based Functional Assignment: The 1.2 Å Crystal Structure of the yjgF Gene Product from *Escherichia coli*," *Protein Science* 8:2428-2437 (1999).

Wagner, et al., "The Free Radical in Pyruvate Formate-Lyase Is Located on Glycine-734," *Proc. Natl. Acad. Sci. USA* 89:996-1000 (1992).

Walmsley, et al., "8-Anilino-1-Naphthalenesulfonate Is a Fluorescent Probe of Conformational Changes in the D-Galactose-$H^+$ Simport Protein of *Escherichia coli*," *J. Biol. Chem.*269:17009-17019 (1994).

Walton, et al., "Nucleotide Sequence of the *Escherichia coli* Uridine Phosphorylase (*udp*) Gene," *Nucleic Acids Res.* 17:6741 (1989).

Wasinger, et al., "Small Genes/Gene-Products in *Escherichia coli* K-12," *FEMS Microbiol. Lett.* 169:375-382 (1998).

Wente, et al., "Different Amino Acid Substitutions at the Same Position in the Nucleotide-Binding Site of Aspartate Transcarbamoylase Have Diverse Effects on the Allosteric Properties of the Enzyme," *J. Biol. Chem.* 266:20833-20839 (1991).

Wong, et al., "Transcription of *pfl* Is Regulatred by Anaerobiosis, Catabolite Repression, Pyruvate, and *oxrA*: *pfl*::MU dA Operon Fusions of *Salmonella typhimurium*," *J. Bacteriol.* 171:4900-4905 (1989).

Wyborn, et al., "Expression of the *Escherichia coli yfiD* Gene Responds to Intracellular pH and Reduces the Accumulation of Acidic Metabolic End Products," *Microbiology* 148:1015-1026 (2002).

Yano, et al., "Directed Evolution of an Aspartate Aminotransferase with New Substrate Specificities," *Proc. Natl. Acad. Sci. USA* 95:5511-5515 (1998).

Yoshida, et al., "Physical Map Location of a Set of *Escherichia coli* Genes (*hde*) Whose Expression Is Affected by the Nucleoid Protein H-NS," *J. Bacteriol.* 175:7747-7748 (1993).

Abstract of Reference B1, WO 99/18228.
Abstract of Reference B3, WO 01/05939.
Abstract of Reference B39, DE 101 32 946.
Abstract of Reference B40, DE 101 35 053.
World Intellectual Property Association, International Preliminary Report on Patentability for International Application No. PCT/EP2005/000767, Aug. 7, 2006.

* cited by examiner

Figure 1: Map of plasmid pTrc99AyibD
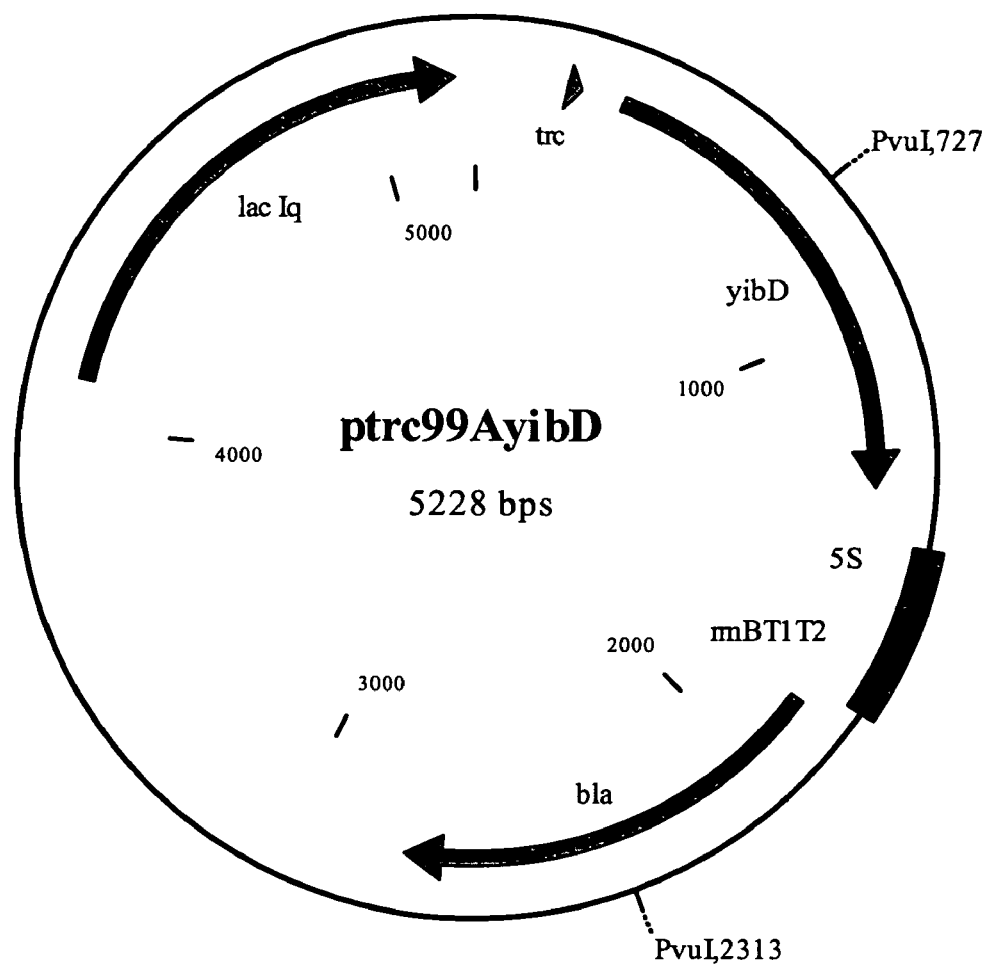

SEQUENCE LISTING

```
<160> NUMBER OF SEQ ID NOS: 6

<210> SEQ ID NO 1
<211> LENGTH: 31
<212> TYPE: DNA
<213> ORGANISM: Artificial sequence
<220> FEATURE:
<221> NAME/KEY: Primer
<222> LOCATION: (1)..(31)
<223> OTHER INFORMATION: yibD-ex1

<400> SEQUENCE: 1
gatctagagc tcgtcaggat aacttcagag g                           31

<210> SEQ ID NO 2
<211> LENGTH: 32
<212> TYPE: DNA
<213> ORGANISM: Artificial sequence
<220> FEATURE:
<221> NAME/KEY: Primer
<222> LOCATION: (1)..(32)
<223> OTHER INFORMATION: yibD-ex2

<400> SEQUENCE: 2
gatctaagct tagcccgaag cggcgaagtt ta                          32

<210> SEQ ID NO 3
<211> LENGTH: 1114
<212> TYPE: DNA
<213> ORGANISM: Escherichia coli
<220> FEATURE:
<221> NAME/KEY: PCR product
<222> LOCATION: (1)..(1114)
<223> OTHER INFORMATION: yibD PCR product
<220> FEATURE:
```

-continued

```
<221> NAME/KEY: CDS
<222> LOCATION: (45)..(1079)
<223> OTHER INFORMATION: yibD coding region
<220> FEATURE:
<221> NAME/KEY: primer_bind
<222> LOCATION: (1)..(31)
<223> OTHER INFORMATION: Primer yibD-ex1
<220> FEATURE:
<221> NAME/KEY: primer_bind
<222> LOCATION: (1083)..(1114)
<223> OTHER INFORMATION: Primer yibD-ex2

<400> SEQUENCE: 3
```

| | | |
|---|---|---|
| gatctagagc tcgtcaggat aacttcagag gtcgtcggta attt atg atg aac agc<br>                                                 Met Met Asn Ser<br>                                                  1 | | 56 |
| acc aat aaa ctt agt gtt att att ccg tta tat aat gcg ggc gat gat<br>Thr Asn Lys Leu Ser Val Ile Ile Pro Leu Tyr Asn Ala Gly Asp Asp<br> 5                  10                  15                  20 | | 104 |
| ttc cgc act tgt atg gaa tct tta att acg caa acc tgg act gct ctg<br>Phe Arg Thr Cys Met Glu Ser Leu Ile Thr Gln Thr Trp Thr Ala Leu<br>             25                  30                  35 | | 152 |
| gaa atc att att att aac gat ggt tca acg gat aat tct gtt gaa ata<br>Glu Ile Ile Ile Ile Asn Asp Gly Ser Thr Asp Asn Ser Val Glu Ile<br>         40                  45                  50 | | 200 |
| gca aag tat tac gca gaa aac tat ccg cac gtt cgt ttg ttg cat cag<br>Ala Lys Tyr Tyr Ala Glu Asn Tyr Pro His Val Arg Leu Leu His Gln<br>     55                  60                  65 | | 248 |
| gcg aat gct ggc gca tcg gtg gcg cgt aat cgt ggg att gaa gtg gca<br>Ala Asn Ala Gly Ala Ser Val Ala Arg Asn Arg Gly Ile Glu Val Ala<br>  70                  75                  80 | | 296 |
| acg ggc aaa tat gtc gct ttt gtc gat gct gac gat gaa gtc tat ccc<br>Thr Gly Lys Tyr Val Ala Phe Val Asp Ala Asp Asp Glu Val Tyr Pro<br>85                  90                  95                 100 | | 344 |
| acc atg tac gaa acg ctg atg acc atg gcg tta gag gac gac ctc gac<br>Thr Met Tyr Glu Thr Leu Met Thr Met Ala Leu Glu Asp Asp Leu Asp<br>                105                 110                 115 | | 392 |
| gtg gcg cag tgc aac gct gac tgg tgt ttt cgt gaa acg gga gaa acc<br>Val Ala Gln Cys Asn Ala Asp Trp Cys Phe Arg Glu Thr Gly Glu Thr<br>            120                 125                 130 | | 440 |
| tgg caa tcc atc ccc acc gat cgc ctt cgc tca acc ggc gta tta acc<br>Trp Gln Ser Ile Pro Thr Asp Arg Leu Arg Ser Thr Gly Val Leu Thr<br>        135                 140                 145 | | 488 |
| ggc ccg gac tgg ctg cgg atg ggg ctt tct tcg cgc cgt tgg act cac<br>Gly Pro Asp Trp Leu Arg Met Gly Leu Ser Ser Arg Arg Trp Thr His<br>    150                 155                 160 | | 536 |
| gtt gtc tgg atg ggg gtt tat cgc cgt gat gtt att gtt aaa aat aac<br>Val Val Trp Met Gly Val Tyr Arg Arg Asp Val Ile Val Lys Asn Asn<br>165                 170                 175                 180 | | 584 |
| att aaa ttt att gcc gga tta cat cat cag gat att gtc tgg aca aca<br>Ile Lys Phe Ile Ala Gly Leu His His Gln Asp Ile Val Trp Thr Thr<br>                185                 190                 195 | | 632 |
| gaa ttc atg ttt aac gcg ctg cgt gcg cga tat acc gag caa tca tta<br>Glu Phe Met Phe Asn Ala Leu Arg Ala Arg Tyr Thr Glu Gln Ser Leu<br>            200                 205                 210 | | 680 |
| tat aaa tat tat ctg cat aat acg tca gtg agt cgg ttg cat aga caa<br>Tyr Lys Tyr Tyr Leu His Asn Thr Ser Val Ser Arg Leu His Arg Gln<br>        215                 220                 225 | | 728 |
| ggg aat aaa aac ctt aat tat caa cgt cac tat att aag att acc cgc<br>Gly Asn Lys Asn Leu Asn Tyr Gln Arg His Tyr Ile Lys Ile Thr Arg<br>    230                 235                 240 | | 776 |
| ctg ctg gag aaa tta aat cga aat tat gcc gac aaa att atg att tat | | 824 |

```
Leu Leu Glu Lys Leu Asn Arg Asn Tyr Ala Asp Lys Ile Met Ile Tyr
245                 250                 255                 260 ccg gaa ttt cat cag caa ata act tac gag gca ttg cgt gtt tgc cat      872
Pro Glu Phe His Gln Gln Ile Thr Tyr Glu Ala Leu Arg Val Cys His
                    265                 270                 275 gcg gtg cgc aaa gag ccg gat att ctt acc cgc caa cgg atg att gcc      920
Ala Val Arg Lys Glu Pro Asp Ile Leu Thr Arg Gln Arg Met Ile Ala
                280                 285                 290 gag ata ttt act tcc ggt atg tat aag cgc ctg att acc aat gtg cgc      968
Glu Ile Phe Thr Ser Gly Met Tyr Lys Arg Leu Ile Thr Asn Val Arg
            295                 300                 305 agc gtg aag gtc ggt tac cag gcg tta ctg tgg tct ttc cgc tta tgg     1016
Ser Val Lys Val Gly Tyr Gln Ala Leu Leu Trp Ser Phe Arg Leu Trp
        310                 315                 320 caa tgg cgc gac aaa acg cgg tcg cac cat cgc att acg cgt agc gcc     1064
Gln Trp Arg Asp Lys Thr Arg Ser His His Arg Ile Thr Arg Ser Ala
325                 330                 335                 340 ttt aat ttg cgc tag cgttaaactt cgccgcttcg ggctaagctt agatc           1114
Phe Asn Leu Arg <210> SEQ ID NO 4
<211> LENGTH: 344
<212> TYPE: PRT
<213> ORGANISM: Escherichia coli

<400> SEQUENCE: 4

Met Met Asn Ser Thr Asn Lys Leu Ser Val Ile Ile Pro Leu Tyr Asn
1               5                   10                  15

Ala Gly Asp Asp Phe Arg Thr Cys Met Glu Ser Leu Ile Thr Gln Thr
                20                  25                  30

Trp Thr Ala Leu Glu Ile Ile Ile Asn Asp Gly Ser Thr Asp Asn
            35                  40                  45

Ser Val Glu Ile Ala Lys Tyr Tyr Ala Glu Asn Tyr Pro His Val Arg
        50                  55                  60

Leu Leu His Gln Ala Asn Ala Gly Ala Ser Val Ala Arg Asn Arg Gly
65                  70                  75                  80

Ile Glu Val Ala Thr Gly Lys Tyr Val Ala Phe Val Asp Ala Asp Asp
                85                  90                  95

Glu Val Tyr Pro Thr Met Tyr Glu Thr Leu Met Thr Met Ala Leu Glu
                100                 105                 110

Asp Asp Leu Asp Val Ala Gln Cys Asn Ala Asp Trp Cys Phe Arg Glu
            115                 120                 125

Thr Gly Glu Thr Trp Gln Ser Ile Pro Thr Asp Arg Leu Arg Ser Thr
        130                 135                 140

Gly Val Leu Thr Gly Pro Asp Trp Leu Arg Met Gly Leu Ser Ser Arg
145                 150                 155                 160

Arg Trp Thr His Val Val Trp Met Gly Val Tyr Arg Arg Asp Val Ile
                165                 170                 175

Val Lys Asn Asn Ile Lys Phe Ile Ala Gly Leu His His Gln Asp Ile
            180                 185                 190

Val Trp Thr Thr Glu Phe Met Phe Asn Ala Leu Arg Ala Arg Tyr Thr
        195                 200                 205

Glu Gln Ser Leu Tyr Lys Tyr Tyr Leu His Asn Thr Ser Val Ser Arg
    210                 215                 220

Leu His Arg Gln Gly Asn Lys Asn Leu Asn Tyr Gln Arg His Tyr Ile
225                 230                 235                 240
```

```
Lys Ile Thr Arg Leu Leu Glu Lys Leu Asn Arg Asn Tyr Ala Asp Lys
            245                 250                 255

Ile Met Ile Tyr Pro Glu Phe His Gln Gln Ile Thr Tyr Glu Ala Leu
            260                 265                 270

Arg Val Cys His Ala Val Arg Lys Glu Pro Asp Ile Leu Thr Arg Gln
            275                 280                 285

Arg Met Ile Ala Glu Ile Phe Thr Ser Gly Met Tyr Lys Arg Leu Ile
            290                 295                 300

Thr Asn Val Arg Ser Val Lys Val Gly Tyr Gln Ala Leu Leu Trp Ser
305                 310                 315                 320

Phe Arg Leu Trp Gln Trp Arg Asp Lys Thr Arg Ser His His Arg Ile
            325                 330                 335

Thr Arg Ser Ala Phe Asn Leu Arg
            340

<210> SEQ ID NO 5
<211> LENGTH: 1035
<212> TYPE: DNA
<213> ORGANISM: Salmonella typhimurium
<220> FEATURE:
<221> NAME/KEY: CDS
<222> LOCATION: (1)..(1035)
<223> OTHER INFORMATION: yibD-Orf

<400> SEQUENCE: 5 atg aaa aat agt aaa acc aaa gtg agt atc att gtc ccg tta tat aat      48
Met Lys Asn Ser Lys Thr Lys Val Ser Ile Ile Val Pro Leu Tyr Asn
1               5                   10                  15 gcg gga gcg gat ttt aat gct tgc atg gcg tcg tta atc gcg caa acg      96
Ala Gly Ala Asp Phe Asn Ala Cys Met Ala Ser Leu Ile Ala Gln Thr
            20                  25                  30 tgg tcg gcg ctg gaa att att att gtg aat gat gga tcg acg gat cat     144
Trp Ser Ala Leu Glu Ile Ile Ile Val Asn Asp Gly Ser Thr Asp His
        35                  40                  45 tcc gtt gag ata gca aaa cat tac gcg gaa cat tac cca cat gtt cga     192
Ser Val Glu Ile Ala Lys His Tyr Ala Glu His Tyr Pro His Val Arg
    50                  55                  60 ctg ctt cat cag gcc aat gct ggc gca tct gtc gcc cgt aat ctt ggc     240
Leu Leu His Gln Ala Asn Ala Gly Ala Ser Val Ala Arg Asn Leu Gly
65                  70                  75                  80 ctg caa gcg gcg acc ggc gat tat gtc gcc ttt gtc gat gcg gat gac     288
Leu Gln Ala Ala Thr Gly Asp Tyr Val Ala Phe Val Asp Ala Asp Asp
                85                  90                  95 cag gtc tac ccg aag atg tat gaa acg ctg atg act atg gcg ctt aac     336
Gln Val Tyr Pro Lys Met Tyr Glu Thr Leu Met Thr Met Ala Leu Asn
            100                 105                 110 gat gat ctg gac gtt gcg cag tgt aat gcg gac tgg tgc gtc cga aaa     384
Asp Asp Leu Asp Val Ala Gln Cys Asn Ala Asp Trp Cys Val Arg Lys
        115                 120                 125 acc ggg cac gcc tgg caa tct att ccg acc gat cgt ctg cgt tcc acc     432
Thr Gly His Ala Trp Gln Ser Ile Pro Thr Asp Arg Leu Arg Ser Thr
    130                 135                 140 ggg gta tta agc gga ccg gat tgg ttg cgt atg gcg ttg gcc tcg cgg     480
Gly Val Leu Ser Gly Pro Asp Trp Leu Arg Met Ala Leu Ala Ser Arg
145                 150                 155                 160 cgc tgg acg cat gtt gtc tgg atg ggc gtt tat cga cgt gcg tta att     528
Arg Trp Thr His Val Val Trp Met Gly Val Tyr Arg Arg Ala Leu Ile
                165                 170                 175 acc gat aac aat att act ttc gtt ccc gga cta cat cat cag gac ata     576
Thr Asp Asn Asn Ile Thr Phe Val Pro Gly Leu His His Gln Asp Ile
```

-continued

```
                        180                 185                 190
tta tgg tcg acg gaa gtt atg ttt aat gcc acg cgc gta cgt tat acc        624
Leu Trp Ser Thr Glu Val Met Phe Asn Ala Thr Arg Val Arg Tyr Thr
        195                 200                 205 gaa caa tca tta tat aaa tat ttc ctg cat gat aat tcg gta agc cgt        672
Glu Gln Ser Leu Tyr Lys Tyr Phe Leu His Asp Asn Ser Val Ser Arg
    210                 215                 220 ttg caa aga caa ggc aat aaa aat ctt aat tat cag cgg cat tat att        720
Leu Gln Arg Gln Gly Asn Lys Asn Leu Asn Tyr Gln Arg His Tyr Ile
225                 230                 235                 240 aaa att acg cga tta tta gaa aag ctc aat cgt gat tat gcc cgt cgt        768
Lys Ile Thr Arg Leu Leu Glu Lys Leu Asn Arg Asp Tyr Ala Arg Arg
                245                 250                 255 att ccg att tac ccg gaa ttt cgc cag caa att acc tgg gaa gcg tta        816
Ile Pro Ile Tyr Pro Glu Phe Arg Gln Gln Ile Thr Trp Glu Ala Leu
            260                 265                 270 cgc gtt tgt cat gcg gta cgt aaa gag cct gat att ttg acc cgc cag        864
Arg Val Cys His Ala Val Arg Lys Glu Pro Asp Ile Leu Thr Arg Gln
        275                 280                 285 cgt atg att gcc gaa att ttt act tct ggc atg tat aga cgg atg atg        912
Arg Met Ile Ala Glu Ile Phe Thr Ser Gly Met Tyr Arg Arg Met Met
    290                 295                 300 gct aac gtc cgc agc gcg aaa gca gct tat cag acg ctg ctc tgg tcc        960
Ala Asn Val Arg Ser Ala Lys Ala Ala Tyr Gln Thr Leu Leu Trp Ser
305                 310                 315                 320 ttc cgg ctg tgg caa tgg cgc gac aaa acc ttg tcg cac cgt cgt atg       1008
Phe Arg Leu Trp Gln Trp Arg Asp Lys Thr Leu Ser His Arg Arg Met
                325                 330                 335 gcc cgt aag gcg ctc aat ctg tct tag                                   1035
Ala Arg Lys Ala Leu Asn Leu Ser
            340
```

<210> SEQ ID NO 6
<211> LENGTH: 344
<212> TYPE: PRT
<213> ORGANISM: Salmonella typhimurium

<400> SEQUENCE: 6

```
Met Lys Asn Ser Lys Thr Lys Val Ser Ile Ile Val Pro Leu Tyr Asn
1               5                   10                  15

Ala Gly Ala Asp Phe Asn Ala Cys Met Ala Ser Leu Ile Ala Gln Thr
                20                  25                  30

Trp Ser Ala Leu Glu Ile Ile Val Asn Asp Gly Ser Thr Asp His
            35                  40                  45

Ser Val Glu Ile Ala Lys His Tyr Ala Glu His Tyr Pro His Val Arg
    50                  55                  60

Leu Leu His Gln Ala Asn Ala Gly Ala Ser Val Ala Arg Asn Leu Gly
65                  70                  75                  80

Leu Gln Ala Ala Thr Gly Asp Tyr Val Ala Phe Val Asp Ala Asp Asp
                85                  90                  95

Gln Val Tyr Pro Lys Met Tyr Glu Thr Leu Met Thr Met Ala Leu Asn
                100                 105                 110

Asp Asp Leu Asp Val Ala Gln Cys Asn Ala Asp Trp Cys Val Arg Lys
            115                 120                 125

Thr Gly His Ala Trp Gln Ser Ile Pro Thr Asp Arg Leu Arg Ser Thr
    130                 135                 140

Gly Val Leu Ser Gly Pro Asp Trp Leu Arg Met Ala Leu Ala Ser Arg
145                 150                 155                 160
```

-continued

```
Arg Trp Thr His Val Val Trp Met Gly Val Tyr Arg Arg Ala Leu Ile
            165              170              175

Thr Asp Asn Asn Ile Thr Phe Val Pro Gly Leu His His Gln Asp Ile
            180              185              190

Leu Trp Ser Thr Glu Val Met Phe Asn Ala Thr Arg Val Arg Tyr Thr
        195              200              205

Glu Gln Ser Leu Tyr Lys Tyr Phe Leu His Asp Asn Ser Val Ser Arg
        210              215              220

Leu Gln Arg Gln Gly Asn Lys Asn Leu Asn Tyr Gln Arg His Tyr Ile
225              230              235              240

Lys Ile Thr Arg Leu Leu Glu Lys Leu Asn Arg Asp Tyr Ala Arg Arg
                245              250              255

Ile Pro Ile Tyr Pro Glu Phe Arg Gln Gln Ile Thr Trp Glu Ala Leu
            260              265              270

Arg Val Cys His Ala Val Arg Lys Glu Pro Asp Ile Leu Thr Arg Gln
            275              280              285

Arg Met Ile Ala Glu Ile Phe Thr Ser Gly Met Tyr Arg Arg Met Met
        290              295              300

Ala Asn Val Arg Ser Ala Lys Ala Ala Tyr Gln Thr Leu Leu Trp Ser
305              310              315              320

Phe Arg Leu Trp Gln Trp Arg Asp Lys Thr Leu Ser His Arg Arg Met
                325              330              335

Ala Arg Lys Ala Leu Asn Leu Ser
            340
```

PROCESS FOR L-AMINO ACID PRODUCTION USING ENTEROBACTERIACEAE STRAINS WITH ENHANCED YIBD

CROSS REFERENCE TO RELATED APPLICATIONS

The present application claims priority to German application 10 2004 005 836.9, filed on Feb. 6, 2004, which is incorporated in its entirety herein by reference.

FIELD OF THE INVENTION

The invention relates to a process for the preparation of L-amino acids, especially L-threonine, using strains of the family Enterobacteriaceae in which the open reading frame (ORF) denoted by yibD is enhanced.

BACKGROUND

L-amino acids, especially L-threonine, are used in human medicine and in the pharmaceutical industry, in the food industry and very particularly in animal nutrition.

It is known to prepare L-amino acids by the fermentation of strains of Enterobacteriaceae, especially *Escherichia coli* (*E. coli*) and *Serratia marcescens*. Because of their great importance, attempts are constantly being made to improve the preparative processes. Improvements to the processes may relate to measures involving the fermentation technology, e.g. stirring and oxygen supply, or the composition of the nutrient media, e.g. the sugar concentration during fermentation, or the work-up to the product form, e.g. by ion exchange chromatography, or the intrinsic productivity characteristics of the microorganism itself.

The productivity characteristics of these microorganisms are improved by using methods of mutagenesis, selection and mutant choice to give strains that are resistant to antimetabolites, e.g. the threonine analogue α-amino-β-hydroxyvaleric acid (AHV), or auxotrophic for metabolites of regulatory significance, and produce L-amino acids, e.g. L-threonine.

Methods of recombinant DNA technology have also been used for some years to improve L-amino acid-producing strains of the family Enterobacteriaceae by amplifying individual amino acid biosynthesis genes and studying the effect on production. A survey of the cellular and molecular biology of *Escherichia coli* and *Salmonella* can be found in Neidhardt (ed.): *Escherichia coli* and *Salmonella*, Cellular and Molecular Biology, 2nd edition, ASM Press, Washington D.C., USA (1996).

OBJECT OF THE INVENTION

The object which the inventors set themselves was to provide novel procedures for improving the preparation of L-amino acids, especially L-threonine, by fermentation.

BRIEF DESCRIPTIOIN OF THE FIGURES

FIG. 1: Map of plasmid pTrc99AyibD containing the yibD gene

The indicated lengths are to be understood as approximate. The abbreviations and symbols used are defined as follows:
bla: gene coding for ampicillin resistance
lac Iq: gene for the repressor protein of the trc promoter
tre: trc promoter region, IPTG-inducible
yibD: coding region of the yibD gene
5S: 5S rRNA region
rrnBT: rRNA terminator region The abbreviations for the restriction enzymes are defined as follows:
PvuI: restriction endonuclease from Proteus vulgaris.

SUMMARY OF THE INVENTION

The invention provides a fermentation process for the preparation of L-amino acids, especially L-threonine, using microorganisms of the family Enterobacteriaceae which, in particular, already produce L-amino acids and in which at least the yibD open reading frame, or a nucleotide sequence coding for its gene product, or its alleles, is (are) enhanced.

DETAILED DESCRIPTION OF THE INVENTION

The term "L-amino acids" or "amino acids" mentioned hereafter is understood as meaning one or more amino acids, including their salts, selected from the group comprising L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-threonine is particularly preferred.

In this context the term "enhancement" describes the increase, in a microorganism, of the intracellular activity or concentration of one or more enzymes or proteins encoded by the appropriate DNA, for example by increasing the copy number of the gene(s) or ORF(S) by at least one (1) copy, using a strong promoter or a gene, allele or ORF coding for an appropriate enzyme or protein with a high activity, and optionally combining these measures.

Open reading frame (ORF) is understood as meaning a segment of a nucleotide sequence that codes or can code for a protein/polypeptide or ribonucleic acid to which no function can be assigned according to the state of the art. After a function has been assigned to the segment of nucleotide sequence in question, it is generally referred to as a gene. Alleles are generally understood as meaning alternative forms of a given gene. The forms are distinguished by differences in the nucleotide sequence.

Gene product is generally understood as meaning the protein encoded by a nucleotide sequence, i.e. an ORF, a gene or an allele, or the encoded ribonucleic acid.

Through the measures of enhancement, especially overexpression, the activity or concentration of the appropriate protein is generally increased at least by 10%, 25%, 50%, 75%, 100%, 150%, 200%, 300%, 400% or 500%, and at most by up to 1000% or 2000%, based on the activity or concentration of the wild-type protein or that of the protein in the starting microorganism. Starting microorganism or parent strain is understood as meaning the microorganism on which the measures according to the invention are performed.

The invention provides a process for the preparation of L-amino acids by the fermentation of recombinant microorganisms of the family Enterobacteriaceae, characterized in that
a) the desired L-amino acid-producing microorganisms in which the yibD open reading frame, or nucleotide sequences coding for the gene product, or alleles, is (are) enhanced and, in particular, overexpressed are cultivated in a medium under conditions in which the desired L-amino acid is enriched in the medium or in the cells, and
b) the desired L-amino acid is isolated, constituents of the fermentation broth, and/or all or part ($\geq$0 to 100%) of the biomass, optionally remaining in the isolated product or being completely removed.

The microorganisms, especially recombinant microorganisms, also provided by the present invention can produce L-amino acids from glucose, sucrose, lactose, fructose, maltose, molasses, optionally starch or optionally cellulose, or from glycerol and ethanol. Said microorganisms are representatives of the family Enterobacteriaceae selected from the genera *Escherichia*, *Erwinia*, *Providencia* and *Serratia*. The genera *Escherichia* and *Serratia* are preferred. The species *Escherichia coli* and *Serratia marcescens* may be mentioned in particular among the genera *Escherichia* and *Serratia* respectively.

Recombinant microorganisms are generally produced by transformation, transduction or conjugation with a vector carrying the desired gene.

Examples of suitable strains, particularly L-threonine-producing strains, of the genus *Escherichia*, and especially of the species *Escherichia coli*, are:

| | |
|---|---|
| *Escherichia coli* H4581 | (EP 0 301 572) |
| *Escherichia coli* KY10935 | (Bioscience, Biotechnology and Biochemistry 61 (11), 1877-1882 (1997)) |
| *Escherichia coli* VNIIgenetika MG442 | (U.S. Pat. No. 4,278,765) |
| *Escherichia coli* VNIIgenetika M1 | (U.S. Pat. No. 4,321,325) |
| *Escherichia coli* VNIIgenetika 472T23 | (U.S. Pat. No. 5,631,157) |
| *Escherichia coli* BKIIM B-3996 | (U.S. Pat. No. 5,175,107) |
| *Escherichia coli* kat 13 | (WO 98/04715) |
| *Escherichia coli* KCCM-10132 | (WO 00/09660) |

Examples of suitable L-threonine-producing strains of the genus *Serratia*, and especially of the species *Serratia marcescens*, are:

*Serratia marcescens* HNr21 (Applied and Environmental Microbiology 38(6), 1045-1051 (1979))

*Serratia marcescens* TLrl56 (Gene 57(2-3), 151-158 (1987))

*Serratia marcescens* T-2000 (Applied Biochemistry and Biotechnology 37(3), 255-265 (1992))

L-threonine-producing strains of the family Enterobacteriaceae preferably possess, inter alia, one or more genetic or phenotypic characteristics selected from the group comprising resistance to α-amino-β-hydroxyvaleric acid, resistance to thialysine, resistance to ethionine, resistance to α-methylserine, resistance to diaminosuccinic acid, resistance to α-aminobutyric acid, resistance to borrelidine, resistance to cyclopentanecarboxylic acid, resistance to rifampicin, resistance to valine analogues such as valine hydroxamate, resistance to purine analogues such as 6-dimethylaminopurine, need for L-methionine, optionally partial and compensable need for L-isoleucine, need for meso-diaminopimelic acid, auxotrophy in respect of threonine-containing dipeptides, resistance to L-threonine, resistance to threonine raffinate, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, optionally capability for sucrose utilization, enhancement of the threonine operon, enhancement of homoserine dehydrogenase I-aspartate kinase I, preferably of the feedback-resistant form, enhancement of homoserine kinase, enhancement of threonine synthase, enhancement of aspartate kinase, optionally of the feedback-resistant form, enhancement of aspartate semialdehyde dehydrogenase, enhancement of phosphoenolpyruvate carboxylase, optionally of the feedback-resistant form, enhancement of phosphoenolpyruvate synthase, enhancement of transhydrogenase, enhancement of the RhtB gene product, enhancement of the RhtC gene product, enhancement of the YfiK gene product, enhancement of a pyruvate carboxylase and attenuation of acetic acid formation.

It has been found that the production of L-amino acids, especially L-threonine, by microorganisms of the family Enterobacteriaceae is improved after overexpression of the yibD gene or open reading frame (ORF), or its alleles.

The nucleotide sequences of the genes or open reading frames (ORFs) of *Escherichia coli* belong to the state of the art and can be taken from the genome sequence of *Escherichia coli* published by Blattner et al. (Science 277, 1453-1462 (1997)). It is known that the N-terminal amino acid methionine can be split off by host-specific enzymes (methionine aminopeptidase).

The yibD ORF of *Escherichia coli* K12 is described inter alia by the following data:

| | |
|---|---|
| Name: | open reading frame |
| Function: | putative glycosyl transferase |
| Description: | the yibD open reading frame codes for a 40.5 kDa protein; the isoelectric point is 9.4; the yibD ORF is located on a chromosome e.g. in the case of *Escherichia coli* K12 MG1655 in the intergenic region of the yibQ open reading frame coding for a hypothetical protein, and the tdh gene coding for threonine dehydrogenase |
| Reference: | Blattner et al., Science 277(5331), 1453-1474 (1997) |
| Accession no.: | AE000439 |
| Alternative gene name: | b3615 |

The nucleic acid sequences can be taken from the data banks of the National Center for Biotechnology Information (NCBI) of the National Library of Medicine (Bethesda, Md., USA), the nucleotide sequence data bank of the European Molecular Biologies Laboratories (EMBL, Heidelberg, Germany, or Cambridge, UK) or the DNA data bank of Japan (DDBJ, Mishima, Japan).

For greater clarity, the known sequence of the yibD ORF of *Escherichia coli* is shown as SEQ ID No. 3 and the known sequence of the yibD ORF of *Salmonella typhimurium* is shown as SEQ ID No. 5. The proteins encoded by these reading frames are shown as SEQ ID No. 4 and SEQ ID No. 6.

The open reading frames described in the cited literature references can be used according to the invention. It is also possible to use alleles of the genes, or open reading frames, which result from the degeneracy of the genetic code or from neutral sense mutations. The use of endogenous genes or endogenous open reading frames is preferred.

The term "endogenous genes" or "endogenous nucleotide sequences" is understood as meaning the genes, open reading frames or alleles, or nucleotide sequences, present in the population of a species.

Alleles containing neutral sense mutations include, inter alia, those which result in at least one conservative amino acid exchange in the protein encoded by them.

In the case of aromatic amino acids, one refers to conservative exchanges when phenylalanine, tryptophan and tyrosine are exchanged for one another. In the case of hydrophobic amino acids, one refers to conservative exchanges when leucine, isoleucine and valine are exchanged for one another. In the case of polar amino acids, one refers to conservative exchanges when glutamine and asparagine are exchanged for one another. In the case of basic amino acids, one refers to conservative exchanges when arginine, lysine and histidine are exchanged for one another. In the case of acidic amino acids, one refers to conservative exchanges when aspartic acid and glutamic acid are exchanged for one another. In the case of amino acids containing hydroxyl groups, one refers to conservative exchanges when serine and threonine are exchanged for one another.

Likewise, it is also possible to use nucleotide sequences that code for variants of said proteins which additionally comprise a lengthening or shortening by at least one (1) amino acid at the N or C terminus. This lengthening or shortening amounts to no more than 50, 40, 30, 20, 10, 5, 3 or 2 amino acids or amino acid residues.

Suitable alleles also include those coding for proteins in which at least one (1) amino acid is inserted (insertion) or deleted (deletion). The maximum number of such changes, called indels, can affect 2, 3, 5, 10 or 20 amino acids, but under no circumstances more than 30 amino-acids.

Suitable alleles also include those obtainable by hybridization, especially under stringent conditions, using SEQ ID No. 3 or SEQ ID No. 5 or portions thereof, especially the coding regions or the sequences complementary thereto.

Those skilled in the art will find instructions on the identification of DNA sequences by means of hybridization in, inter alia, the handbook "The DIG System User's Guide for Filter Hybridization" from Boehringer Mannheim GmbH (Mannheim, Germany, 1993) and in Liebl et al. (International Journal of Systematic Bacteriology 41, 255-260 (1991)). The hybridization takes place under stringent conditions, i.e. the only hybrids formed are those in which the probe and the target sequence, i.e. the polynucleotides treated with the probe, are at least 70% identical. It is known that the stringency of the hybridization, including the washing steps, is influenced or determined by varying the buffer composition, the temperature and the salt concentration. The hybridization reaction is generally carried out at relatively low stringency compared with the washing steps (Hybaid Hybridisation Guide, Hybaid Limited, Teddington, UK, 1996).

The hybridization reaction can be carried out using e.g. a buffer corresponding to 5×SSC buffer at a temperature of approx. 50° C.-68° C. It is also possible here to hybridize probes with polynucleotides that are less than 70% identical to the sequence of the probe. Such hybrids are less stable and are removed by washing under stringent conditions. This can be achieved e.g. by lowering the salt concentration to 2×SSC and optionally 0.5×SSC thereafter (The DIG System User's Guide for Filter Hybridisation, Boehringer Mannheim, Mannheim, Germany, 1995), the temperature being set to approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C. or approx. 66° C.-68° C. It is optionally possible to lower the salt concentration to a value corresponding to 0.2×SSC or 0.1× SSC. By gradually increasing the hybridization temperature from 50° C. to 68° C. in steps of approx. 1-2° C., it is possible to isolate polynucleotide fragments that are e.g. at least 70%, at least 80%, at least 90% to 95% or at least 96% to 99% identical to the sequence of the probe used. Further instructions on hybridization are commercially available in kit form (e.g. DIG Easy Hyb from Roche Diagnostics GmbH, Mannheim, Germany, catalogue no. 1603558).

Enhancement can be achieved for example by increasing the expression of the genes, open reading frames or alleles or enhancing the catalytic properties of the protein. Both measures may optionally be combined.

Overexpression can be achieved for example by increasing the copy number of the appropriate genes or open reading frames or mutating the promoter and regulatory region or the ribosome binding site located upstream from the structural gene. Expression cassettes incorporated upstream from the structural gene work in the same way. Inducible promoters additionally make it possible to increase expression in the course of L-threonine production by fermentation. Measures for prolonging the life of the mRNA also improve expression. Furthermore, the enzyme activity is also enhanced by preventing degradation of the enzyme protein. The genes or gene constructs can either be located in plasmids of variable copy number or be integrated and amplified in the chromosome. Alternatively, it is also possible to achieve overexpression of the genes in question by changing the composition of the media and the culture technique.

Those skilled in the art will find relevant instructions inter alia in Chang and Cohen (Journal of Bacteriology 134, 1141-1156 (1978)), Harley and Gregori (Gene 13, 347-353 (1981)), Amann and Brosius (Gene 40, 183-190 (1985)), de Broer et al. (Proceedings of the National Academy of Sciences of the United States of America 80, 21-25 (1983)), LaVallie et al. (BIO/TECHNOLOGY 11, 187-193 (1993)), PCT/US97/13359, Llosa et al. (Plasmid 26, 222-224 (1991)), Quandt and Klipp (Gene 80, 161-169 (1989)), Hamilton et al. (Journal of Bacteriology 171, 4617-4622 (1989)), Jensen and Hammer (Biotechnology and Bioengineering 58, 191-195 (1998)) and well-known textbooks on genetics and molecular biology.

Plasmid vectors replicable in Enterobacteriaceae, e.g. cloning vectors derived from pACYC184 (Bartolome et al., Gene 102, 75-78 (1991)), pTrc99A (Amann et al., Gene 69, 301-315 (1988)) or pSC101 derivatives (Vocke and Bastia, Proceedings of the National Academy of Sciences USA 80(21), 6557-6561 (1983)), can be used. In one process according to the invention, it is possible to use a strain transformed with a plasmid vector, said plasmid vector carrying at least one nucleotide sequence coding for the yibD ORF or its gene product, or allele.

The term "transformation" is understood as meaning the uptake of an isolated nucleic acid by a host (microorganism).

Also, mutations which affect the expression of the appropriate genes or open reading frames can be transferred to different strains by sequence exchange (Hamilton et al., Journal of Bacteriology 171, 4617-4622 (1989)), conjugation or transduction.

Further details on the concepts of genetics and molecular biology can be found in well-known textbooks on genetics and molecular biology, for example the textbook by Birge (Bacterial and Bacteriophage Genetics, 4th ed., Springer Verlag, New York (USA), 2000), the textbook by Berg, Tymoczko and Stryer (Biochemistry, 5th ed., Freeman and Company, New York (USA), 2002) or the textbook by Sambrook et al. (Molecular Cloning, A Laboratory Manual (3-volume set), Cold Spring Harbor Laboratory Press, Cold Spring Harbor (USA), 2001).

Furthermore, for the production of L-amino acids, especially L-threonine, with strains of the family Enterobacteriaceae, it can be advantageous not only to enhance the yibD open reading frame, but also to enhance one or more enzymes of the known threonine biosynthetic pathway, or enzymes of the anaplerotic metabolism, or enzymes for the production of reduced nicotinamide adenine dinucleotide phosphate, or glycolytic enzymes, or PTS enzymes, or enzymes of sulfur metabolism. The use of endogenous genes is generally preferred.

Thus, for example, one or more genes selected from the group comprising:

the thrABC operon coding for aspartate kinase, homoserine dehydrogenase, homoserine kinase and threonine synthase (U.S. Pat. No. 4,278,765), the pyc gene of *Corynebacterium glutamicum* coding for pyruvate carboxylase (WO 99/18228), the pps gene coding for phosphoenolpyruvate synthase (Niersbach, et al., Molecular and General Genetics 231(2), 332-336 (1992)), the ppc gene coding for phosphoenolpyruvate carboxylase (WO 02/064808), the pntA and pntB genes coding for transhydrogenase (Clarke, et al., European Journal of Biochemistry 158, 647-653 (1986)), the rhtB gene for homoserine resistance (EP-A-0 994 190), the rhtC gene for threonine resistance (EP-A-1 013 765), the thrE gene of *Corynebacterium glutamicum* coding for threonine export protein (WO 01/92545), the gdhA gene coding for glutamate dehydrogenase (McPherson, et al., Nucleic Acids Research 11,5257-5266(1983); Valle, et al., Gene 23, 199-209 (1983)), the pgm gene coding for phosphoglucomutase (WO 03/004598), the fba gene coding for fructose biphosphate aldolase (WO 03/004664), the ptsH gene of the ptsHIcrr operon coding for phosphohistidine protein hexose phosphotransferase of the phosphotransferase system PTS (WO 03/004674), the ptsI gene of the ptsHIcrr operon coding for enzyme I of the phosphotransferase system PTS (WO 03/004674), the crr gene of the ptsHIcrr operon coding for the glucose-specific IIA component of the phosphotransferase system PTS (WO 03/004674), the ptsG gene coding for the glucose-specific IIBC component (WO 03/004670), the lrp gene coding for the regulator of the leucine regulon (WO 03/004665), the fadR gene coding for the regulator of the fad regulon (WO 03/038 106), the iclR gene coding for the regulator of the central intermediary metabolism (WO 03/038106), the ahpC gene of the ahpCF operon coding for the small subunit of alkyl hydroperoxide reductase (WO 03/004663), the ahpF gene of the ahpCF operon coding for the large subunit of alkyl hydroperoxide reductase (WO 03/004663), the cysK gene coding for cysteine synthase A (WO 03/006666), the cysB gene coding for the regulator of the cys regulon (WO 03/006666), the cysJ gene of the cysJIH operon coding for the flavoprotein of NADPH sulfite reductase (WO 03/006666), the cysI gene of the cysJIH operon coding for the haemoprotein of NADPH sulfite reductase (WO 03/006666), the cysH gene of the cysJIH operon coding for adenylyl sulfate reductase (WO 03/006666), the rseA gene of the rseABC operon coding for a membrane protein with anti-sigmaE activity (WO 03/008612), the rseC gene of the rseABC operon coding for a global regulator of the sigmaB factor (WO 03/008612), the sucA gene of the sucABCD operon coding for the decarboxylase subunit of 2- ketoglutarate dehydrogenase (WO 03/008614), the sucB gene of the sucABCD operon coding for the dihydrolipoyl transsuccinase E2 subunit of 2-ketoglutarate dehydrogenase (WO 03/008614), the sucC gene of the sucABCD operon coding for the β subunit of succinyl CoA synthetase (WO 03/008615), the sucD gene of the sucABCD operon coding for the α subunit of succinyl CoA synthetase (WO 03/008615), the aceE gene coding for the E1 component of the pyruvate dehydrogenase complex (WO 03/076635), the aceF gene coding for the E2 component of the pyruvate dehydrogenase complex (WO 03/076635), and the rseB gene coding for the regulator of sigmaE factor activity (Missiakas, et al., Molecular Microbiology 24(2), 355-37 1 (1997)) can be simultaneously enhanced and, in particular, overexpressed.

Furthermore, for the production of L-amino acids, especially L-threonine, it can be advantageous not only to enhance the yibD open reading frame, but also to attenuate and, in particular, switch off one or more genes selected from the group comprising:

the tdh gene coding for threonine dehydrogenase (Ravnikar, et al., Journal of Bacteriology 169, 4716-4721 (1987)), the mdh gene coding for malate dehydrogenase (E.C. 1.1.1.37) (Vagel, et al., Archives in Microbiology 149, 36-42 (1987)), the gene product of the yjfA open reading frame (ORF) (Accession Number AAC77180 of the National Center for Biotechnology Information (NCBI, Bethesda, Md., USA), WO 02/29080), the gene product of the ytfP open reading frame (ORF) (Accession Number AAC77179 of the National Center for Biotechnology Information (NCBI, Bethesda, Md., USA), WO 02/29080), the pckA gene coding for the enzyme phosphoenolpyruvate carboxykinase (WO 02/29080), the poxB gene coding for pyruvate oxidase (WO 02/36797), the dgsA gene coding for the DgsA regulator of the phosphotransferase system (WO 02/081721), which is also known as the mlc gene, the fruR gene coding for the fructose repressor (WO 02/081698), which is also known as the cra gene, the rpoS gene coding for the sigma$^{38}$ factor (WO 01/05939), which is also known as the katF gene, and the aspA gene coding for aspartate ammonium lyase (WO 03/008603), or reduce the expression.

In this context the term "attenuation" describes the decrease or switching-off of the intracellular activity or concentration, in a microorganism, of one or more enzymes/proteins encoded by the appropriate DNA, for example by using a weak promoter or a gene or allele which codes for an appropriate enzyme/protein with a low activity, or inactivating the appropriate enzyme/protein, the open reading frame or the gene, and optionally combining these measures.

The attenuation measures generally reduce the activity or concentration of the appropriate protein to 0 to 75%, 0 to 50%, 0 to 25%, 0 to 10% or 0 to 5% of the activity or concentration of the wild-type protein or of the activity or concentration of the protein in the starting microorganism.

Furthermore, for the production of L-amino acids, especially L-threonine, it can be advantageous not only to enhance the yibD open reading frame, but also to switch off unwanted secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms prepared according to the invention can be cultivated by the batch process, the fed batch process or the repeated fed batch process. A summary of known cultivation methods is provided in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Brunswick/Wiesbaden, 1994)).

The culture medium to be used must appropriately meet the demands of the particular strains. Descriptions of culture media for various microorganisms are contained in "Manual of Methods for General Bacteriology" of the American Society for Bacteriology (Washington D.C., USA, 1981).

Carbon sources which can be used are sugars and carbohydrates, e.g. glucose, sucrose, lactose, fructose, maltose, molasses, starch and optionally cellulose, oils and fats, e.g. soya oil, sunflower oil, groundnut oil and coconut fat, fatty acids, e.g. palmitic acid, stearic acid and linoleic acid, alcohols, e.g. glycerol and ethanol, and organic acids, e.g. acetic acid. These substances can be used individually or as a mixture.

Nitrogen sources which can be used are organic nitrogen compounds such as peptones, yeast extract, meat extract, malt extract, corn steep liquor, soya bean flour and urea, or inorganic compounds such as ammonium sulfate, ammonium chloride, ammonium phosphate, ammonium carbonate and ammonium nitrate. The nitrogen sources can be used individually or as a mixture.

Phosphorus sources which can be used are phosphoric acid, potassium dihydrogenphosphate or dipotassium hydrogenphosphate or the corresponding sodium salts. The culture medium must also contain metal salts, e.g. magnesium sulfate or iron sulfate, which are necessary for growth. Finally, essential growth-promoting substances such as amino acids and vitamins can be used in addition to the substances mentioned above. Suitable precursors can also be added to the culture medium. Said feed materials can be added to the culture medium all at once or fed in appropriately during cultivation.

The fermentation is generally carried out at a pH of 5.5 to 9.0, especially of 6.0 to 8.0. The pH of the culture is controlled by the appropriate use of basic compounds such as sodium hydroxide, potassium hydroxide, ammonia or aqueous ammonia, or acidic compounds such as phosphoric acid or sulfuric acid. Foaming can be controlled using antifoams such as fatty acid polyglycol esters. The stability of plasmids can be maintained by adding suitable selectively acting substances, e.g. antibiotics, to the medium. Aerobic conditions are maintained by introducing oxygen or oxygen-containing gaseous mixtures, e.g. air, into the culture. The temperature of the culture is normally 25° C. to 45° C. and preferably 30° C. to 40° C. The culture is continued until the formation of L-amino acids or L-threonine has reached a maximum. This objective is normally achieved within 10 hours to 160 hours.

L-amino acids can be analyzed by means of anion exchange chromatography followed by ninhydrin derivation, as described by Spackman et al. (Analytical Chemistry 30, 1190-1206 (1958)), or by reversed phase HPLC, as described by Lindroth et al. (Analytical Chemistry 51, 1167-1174 (1979)).

The process according to the invention is used to prepare L-amino acids, for example L-threonine, L-isoleucine, L-valine, L-methionine, L-homoserine and L-lysine, especially L-threonine, by fermentation.

The present invention is illustrated in greater detail below with the aid of Examples.

The minimum medium (M9) and complete medium (LB) used for *Escherichia coli* are described by J. H. Miller (A Short Course in Bacterial Genetics (1992), Cold Spring Harbor Laboratory Press). The isolation of plasmid DNA from *Escherichia coli* and all the techniques for restriction, ligation, Klenow treatment and alkaline phosphatase treatment are carried out according to Sambrook et al. (Molecular Cloning—A Laboratory Manual (1989), Cold Spring Harbor Laboratory Press). Unless described otherwise, the transformation of *Escherichia coli* is carried out according to Chung et al. (Proceedings of the National Academy of Sciences of the United States of America 86, 2172-2175 (1989)).

The incubation temperature in the preparation of strains and transformants is 37° C.

EXAMPLE 1

Construction of Expression Plasmid pTrc99AyibD

The yibD gene from *E. coli* K12 is amplified using the polymerase chain reaction (PCR) and synthetic oligonucleotides. The nucleotide sequence of the yibD gene in *E. coli* K12 MG1655 (Accession Number AE000439, Blattner et al. (Science 277, 1453-1474 (1997))) is used as the starting material to synthesize PCR primers (MWG Biotech, Ebersberg, Germany). The sequences of the primers are modified to provide recognition sites for restriction enzymes. The recognition sequence for SacI is chosen for the yibD-ex1 primer and the recognition sequence for HindIII is chosen for the yibD-ex2 primer, said sequences being underlined in the nucleotide sequences shown below:

```
yibD-ex1:                              (SEQ ID No. 1)
5'-GATCTAGAGCTCGTCAGGATAACTTCAGAGG-3' yibD-ex2:                              (SEQ ID No. 2)
5'-GATCTAAGCTTAGCCCGAAGCGGCGAAGTTTA-3'
```

The chromosomal *E. coli* K12 MG1655 DNA used for the PCR is isolated with "Qiagen Genomic-tips 100/G" (QIAGEN, Hilden, Germany) in accordance with the manufacturer's instructions. An approx. 1114 bp DNA fragment can be amplified with the specific primers under standard PCR conditions (Innis et al. (1990), PCR Protocols. A Guide to Methods and Applications, Academic Press) using Vent DNA polymerase (New England Biolabs GmbH, Frankfurt, Germany) (SEQ ID No. 3).

The amplified yibD fragment is ligated with vector pCR-Blunt II-TOPO (Zero TOPO TA Cloning Kit, Invitrogen, Groningen, The Netherlands) in accordance with the manufacturer's instructions and transformed into the *E. coli* strain TOP10. Plasmid-carrying cells are selected on LB agar supplemented with 50 μg/ml of kanamycin. After isolation of the plasmid DNA, the vector is cleaved with the enzymes PvuI and HindIII/SacI and, after the cleavage has been checked in 0.8% agarose gel, is called pCRBluntyibD.

Vector pCRBluntyibD is then cleaved with the enzymes HindIII and SacI and, after separation in 0.8% agarose gel, the yibD fragment is isolated from the gel (QIAquick Gel Extraction Kit, QIAGEN, Hilden, Germany) and ligated with vector pTrc99A (Pharmacia Biotech, Uppsala, Sweden) which has been digested with the enzymes HindIII and SacI. The *E. coli* strain XL1Blue MRF' (Stratagene, La Jolla, USA) is transformed with the ligation mixture and plasmid-carrying cells are selected on LB agar supplemented with 50 μg/ml of ampicillin.

The success of the cloning can be demonstrated, after isolation of the plasmid DNA, by control cleavage with the enzyme PvuI.

The plasmid is called pTrc99AyibD (FIG. 1).

EXAMPLE 2

Preparation of L-Threonine with the Strain MG442/pTrc99AyibD

The L-threonine-producing *E. coli* strain MG442 is described in U.S. Pat. No. 4,278,765 and is deposited in the Russian National Collection for Industrial Microorganisms (VKPM, Moscow, Russia) as CMIM B-1628.

The strain MG442 is transformed with expression plasmid pTrc99AyibD, described in Example 1, and with vector pTrc99A and plasmid-carrying cells are selected on LB agar supplemented with 50 µg/ml of ampicillin. This procedure yields the strains MG442/pTrc99AyibD and MG442/pTrc99A. Chosen individual colonies are then multiplied further on minimum medium of the following composition: 3.5 g/l of $Na_2HPO_4.2H_2O$, 1.5 g/l of $KH_2PO_4$, 1 g/l of $NH_4Cl$, 0.1 g/l of $MgSO_4.7H_2O$, 2 g/l of glucose, 20 g/l of agar, 50 mg/l of ampicillin. The formation of L-threonine is verified in 10 ml batch cultures contained in 100 ml conical flasks. This is done by inoculating 10 ml of preculture medium of the following composition: 2 g/l of yeast extract, 10 g/l of $(NH_4)_2SO_4$, 1 g/l of $KH_2PO_4$, 0.5 g/l of $MgSO_4.7H_2O$, 15 g/l of $CaCO_3$, 20 g/l of glucose, 50 mg/l of ampicillin, and incubating for 16 hours at 37° C. and 180 rpm on an ESR incubator from Kühner AG (Birsfelden, Switzerland). 250 µl of each of these precultures are transferred to 10 ml of production medium (25 g/l of $(NH_4)_2SO_4$, 2 g/l of $KH_2PO_4$, 1 g/l of $MgSO_4.7H_2O$, 0.03 g/l of $FeSO_4.7H_2O$, 0.018 g/l of $MnSO_4.1H_2O$, 30 g/l of $CaCO_3$, 20 g/l of glucose, 50 mg/l of ampicillin) and incubated for 48 hours at 37° C. The formation of L-threonine by the original strain MG442 is verified in the same way except that no ampicillin is added to the medium. After incubation the optical density (OD) of the culture suspension is determined using an LP2W photometer from Dr. Lange (Düsseldorf, Germany) at a measurement wavelength of 660 nm.

The concentration of L-threonine formed is then determined in the sterile-filtered culture supernatant using an amino acid analyzer from Eppendorf-BioTronik (Hamburg, Germany) by means of ion exchange chromatography and postcolumn reaction with ninhydrin detection.

Table 1 shows the result of the experiment.

TABLE 1

| Strain | OD (660 nm) | L-threonine g/l |
|---|---|---|
| MG442 | 5.6 | 1.4 |
| MG442/pTrc99A | 3 | 1.3 |
| MG442/pTrc99AyibD | 4.6 | 3.0 |

What is claimed is:

1. A process for the preparation of an L-amino acid by the fermentation of a microorganism of the family Enterobacteriaceae, comprising:
   a) cultivating said microorganism in a fermentation medium under conditions in which said L-amino acid is produced, wherein:
      i) said microorganism produces said L-amino acid;
      ii) said microorganism has been engineered to overexpress a polynucleotide encoding a protein comprising the amino acid sequence of either SEQ ID NO:4 or SEQ ID NO:6 by transformed said microorganism with a vector comprising said polynucleotide;
   b) allowing said fermentation medium or said microorganism to become enriched in said L-amino acid; and
   c) isolating and quantitating said L-amino acid.

2. The process of claim 1, wherein some or all of the constituents of said fermentation medium and/or the biomass of said microorganism are isolated along with said L-amino acid.

3. The process of claim 1, wherein said microorganism is selected from the genera *Escherichia, Erwinia, Providencia* and *Serratia*.

4. The process of claim 1, wherein said microorganism is of the species *E. coli*.

5. The process of claim 1, wherein said L-amino acid is selected from the group consisting of: L-isoleucine, L-valine, L-methionine, L-homoserine and L-lysine.

6. The process of claim 1, wherein said L-amino acid is L-threonine.

7. The process of claim 1, wherein in addition to said polynucleotide being overexpressed, at least one additional gene or operon from *E. coli* is overexpressed by a process in which bacteria are transformed with a vector comprising said gene or operon and wherein said gene or operon is selected from the group consisting of:
   a) an tbrABC operon coding for aspartate kinase, homoserine dehydrogenase, homoserine kinase and threonine synthase;
   b) a pyc gene coding for pyruvate carboxylase;
   c) a pps gene coding for phosphoenolpyruvate synthase;
   d) a ppc gene coding for phosphoenolpyruvate carboxylase;
   e) pntA and pntB genes coding for transhydrogenase;
   f) a rhtB gene for homoserine resistance;
   g) a rhtC gene for threonine resistance;
   h) a thrE gene coding for threonine export protein;
   i) a gdhA gene coding for glutamate dehydrogenase;
   j) a pgm gene coding for phosphoglucomutase;
   k) a fba gene coding for fructose biphosphate aldolase;
   l) a ptsH gene coding for phosphohistidine protein hexose phosphotransferase;
   m) a ptsI gene coding for enzyme I of the phosphotransferase system;
   n) a crr gene coding for the glucose-specific IIA component;
   o) a ptsG gene coding for the glucose-specific IIBC component;
   p) a lrp gene coding for the regulator of the leucine regulon;
   q) a fadR gene coding for the regulator of the fad regulon;
   r) an iclR gene coding for the regulator of the central intermediary metabolism,;
   s) an ahpC gene coding for the small subunit of alkyl hydroperoxide reductase;
   t) an ahpF gene coding for the large subunit of alkyl hydroperoxide reductase;

u) a cysK gene coding for cystein synthase A;
v) a cysB gene coding for the regulator of the cys regulon;
w) a cysJ gene coding for the flavoprotein of NADPH sulfite reductase;
x) a cysI gene coding for the haemoprotein of NADPH sulfite reductase;
y) a cysH gene coding for adenylyl sulfate reductase;
z) a rseA gene coding for a membrane protein with anti-sigmaE activity;
aa) a rseC gene coding for a global regulator of the sigmaE factor;
bb) a sucA gene coding for the decarboxylase subunit of 2-ketoglutarate dehydrogenase;
cc) a sucB gene coding for the dihydrolipoyl transsuccinase E2 subunit of 2-ketoglutarate dehydrogenase;
dd) a sucC gene coding for the β subunit of succinyl CoA synthetase;
ee) a sucD gene coding for the α subunit of succinyl CoA synthetase;
ff) an aceE gene coding for the E1 component of the pyruvate dehydrogenase complex;
gg) an aceF gene coding for the E2 component of the pyruvate dehydrogenase complex; and
hh) a rseB gene coding for the regulator of sigmaE factor activity.

8. The process of claim 1, wherein in addition to said polynucleotide being overexpressed, the expression of one or more additional genes from *E. coli* is reduced, said one or more additional genes from *E. coli* being selected from the group consisting of:
   a) a tdh gene coding for threonine dehydrogenase;
   b) a mdh gene coding for malate dehydrogenase;
   c) a gene product of the yjfA open reading frame (ORF);
   d) a gene product of the ytfP open reading frame (ORF);
   e) a pckA gene coding for phosphoenolpyruvate carboxykinase;
   f) a poxB gene coding for pyruvate oxidase;
   g) a dgsA gene coding for the DgsA regulator of the phosphotransferase system;
   h) a rpoS gene coding for the sigma$^{38}$ factor; and
   i) an aspA gene coding for aspartate ammonium lyase.

9. The process of claim 1, wherein said microorganism has been engineered to overexpress a polynucleotide encoding a protein comprising the amino acid sequence of SEQ ID NO:4 by transforming said microrganism with a vector comprising said polynucleotide.

10. The process of claim 9, wherein said protein consists of the amino acid sequence of SEQ ID NO:4.

11. The process of claim 9, wherein said polynucleotide comprises the nucleotide sequence of SEQ ID NO:3.

12. The process of claim 9, wherein said polynucleotide consists of the nucleotide sequence of SEQ ID NO:3.

13. The process of claim 9, wherein the concentration of said protein comprising the amino acid sequence of SEQ ID NO:4 is increased by at least 10%, relative to concentration in said microorganism prior to the overexpression of said protein.

14. The process of claim 9, wherein said microorganism is of the species *E. coli* and said L-amino acid is L-threonine.

15. The process of claim 1, wherein said microorganism has been engineered to overexpress a polynucleotide encoding a protein comprising the amino acid sequence of SEQ ID NO:6 by transforming said microorganism with a vector comprising said polynucleotide.

16. The process of claim 1, wherein said protein consists of the amino acid sequence of SEQ ID NO:6.

17. The process of claim 15, wherein said polynucleotide comprises the nucleotide sequence of SEQ ID NO:5.

18. The process of claim 15, wherein said polynucleotide consists of the nucleotide sequence of SEQ ID NO:5.

19. The process of claim 15, wherein the concentration of said protein comprising the amino acid sequence of SEQ ID NO:6 is increased by at least 10%, relative to concentration in said microorganism prior to the overexpression of said protein.

20. The process of claim 15, wherein said microorganism is of the species *E. coli* and said L-amino acid is L-threonine.

* * * * *

UNITED STATES PATENT AND TRADEMARK OFFICE
CERTIFICATE OF CORRECTION

| | | |
|---|---|---|
| PATENT NO. | : 7,575,905 B2 | Page 1 of 1 |
| APPLICATION NO. | : 10/794417 | |
| DATED | : August 18, 2009 | |
| INVENTOR(S) | : Rieping et al. | |

It is certified that error appears in the above-identified patent and that said Letters Patent is hereby corrected as shown below:

On the cover page, item [*] Notice:   Subject to any disclaimer, the term of this patent is extended or adjusted under 35 USC 154(b) by 622 days Delete the phrase "by 622 days" and insert -- by 732 days --

Signed and Sealed this

Eighth Day of June, 2010

David J. Kappos
*Director of the United States Patent and Trademark Office*